United States Patent [19]

Seiter

[11] Patent Number: 5,151,525
[45] Date of Patent: Sep. 29, 1992

[54] PROCESS FOR PRODUCING 2-OXO-1,3-DIBENZYL-4,5-CIS-IMIDAZOLIDINEDICARBOXYLIC ACID

[75] Inventor: John J. Seiter, Houston, Tex.
[73] Assignee: PPG Industries, Inc., Pittsburgh, Pa.
[21] Appl. No.: 717,146
[22] Filed: Jun. 18, 1991
[51] Int. Cl.$^5$ .......................................... C07D 233/32
[52] U.S. Cl. .................................................... 548/321
[58] Field of Search ........................................ 548/321

[56] References Cited

U.S. PATENT DOCUMENTS

| | | | |
|---|---|---|---|
| 2,489,232 | 11/1949 | Goldberg et al. | 548/321 |
| 2,489,235 | 11/1949 | Goldberg et al. | 548/303 |
| 2,489,238 | 11/1949 | Goldberg et al. | 548/303 |
| 3,700,659 | 10/1972 | Gerecke et al. | 548/303 |
| 4,659,837 | 4/1987 | Trautmann et al. | 548/321 |

FOREIGN PATENT DOCUMENTS

| | | |
|---|---|---|
| 1,180338 | 1/1985 | Canada . |
| 0082396 | 6/1983 | European Pat. Off. ............ 548/321 |
| 1008270 | 1/1976 | Japan . |

OTHER PUBLICATIONS

Lavielle, S. et al, *Journal of the American Chemical Society*, vol. 100, No. 5, pp. 1558–1563 (1978).
Gerecke, M. et al, *Helvetica Chimica Acta*, vol. 53, Fasc. 5, No. 116, pp. 991–999 (1970).

*Primary Examiner*—Patricia L. Morris
*Assistant Examiner*—Lenora Ava Miltenberger
*Attorney, Agent, or Firm*—George D. Morris

[57] ABSTRACT

Alkali metal salt of meso-2,3-bis(benzylamino)succinic acid, phosgene, and alkali metal hydroxide are reacted under alkaline conditions and in the presence of water and anisole in a multi-phase system to form a multi-phase mixture comprising: (1) a liquid aqueous phase having a pH of at least about 7.5 and comprising an aqueous solution of alkali metal salt of 2-oxo-1,3-dibenzyl-4,5-cis-imidazolidinedicarboxylic acid, and (2) a liquid organic phase. The aqueous solution is acidified to precipitate 2-oxo-1,3-dibenzyl-4,5-cis-imidazolidinedicarboxylic acid.

14 Claims, No Drawings

PROCESS FOR PRODUCING 2-OXO-1,3-DIBENZYL-4,5-CIS-IMIDAZOLIDINEDICARBOXYLIC ACID

BACKGROUND OF THE INVENTION

Syntheses of biotin are described in U.S. Pat. No. 2,489,232 and in Lavielle et al, "A Total Synthesis of Biotin . . . ", *Journal of the American Chemical Society*, volume 100, pages 1558–1563 (1978). Several of these syntheses include the step of reacting potassium salt of meso-2,3-bis(benzylamino)succinic acid [the CAS Registry No. of meso-2,3-bis(benzylamino)succinic acid is 55645-40-4] with phosgene and potassium hydroxide in the presence of water and either xylene or toluene. Although the patent and the Lavielle et al paper in their general descriptions refer to reacting the meso-2,3-bis(benzylamino)succinic acid with phosgene and potassium hydroxide, it is clear from the experimental sections that at the high values of pH involved, it is potassium salt of meso-2,3-bis(benzylamino)succinic acid which is reacted with the phosgene and potassium hydroxide. Upon completion of the reaction, the entire reaction mixture is acidified to precipitate 2-oxo-1,3-dibenzyl-4,5-cis-imidazolidinedicarboxylic acid [CAS Registry No. 51591-75-4] (hereinafter referred to for brevity as "cyclo acid") and meso-2,3-bis(benzylamino)succinic acid, the potassium salt of which remained unreacted during the phosgenation reaction. For brevity and in keeping with ordinary chemical usage, such acid is hereinafter referred to as "unreacted meso-2,3-bis(benzylamino)succinic acid." The precipitate is then further processed to separate the unreacted meso-2,3-bis(benzylamino)succinic acid from the desired cyclo acid. The yield of cyclo acid based on the meso-2,3-bis(benzylamino)succinic acid equivalent of its potassium salt in such processes is low as is evidenced by the large amounts of unreacted meso-2,3-bis(benzylamino)succinic acid recovered. For example, the recovered unreacted meso-2,3-bis(benzylamino)succinic acid reported in column 4 of U.S. Pat. No. 2,489,232 amounted to almost 34 percent of the meso-2,3-bis(benzylamino)succinic acid charged. Similarly, the recovered unreacted meso-2,3-bis(benzylamino)succinic acid is reported in the Lavielle et al paper, cited above, as being 20 percent; however calculation shows it to be nearly 23 percent.

More recently it was found that cyclo acid could be produced in higher yields and with less contamination by unreacted meso-2,3-bis(benzylamino)succinic acid by using methylene chloride as the substantially water-immiscible inert organic solvent in the process rather than toluene or xylene. Further improvement was obtained by separating the liquid organic phase and the aqueous phase after phosgenation but before acidification of the aqueous phase.

Although methylene chloride is a satisfactory substantially water-immiscible inert organic solvent from the technical viewpoint, it has come under increasing attack as a volatile environmental pollutant. Since solvents often perform differently in the process and since there are few, if any, general principles which would allow one to predict in advance the utility of one solvent over another, the search is largely empirical in nature.

THE INVENTION

Applicant has discovered that cyclo acid can be produced in high yields and with low contamination by unreacted meso-2,3-bis(benzylamino)succinic acid by using anisole [CAS Registry No. 100-66-3] as the substantially water-immiscible inert organic solvent in the process.

Accordingly, in a process wherein: (a) alkali metal salt of meso-2,3-bis(benzylamino)succinic acid, phosgene, and alkali metal hydroxide are reacted under alkaline conditions and in the presence of water and substantially water-immiscible inert liquid organic solvent in a multi-phase system to form a multi-phase mixture comprising: (1) an aqueous solution of alkali metal salt of 2-oxo-1,3-dibenzyl-4,5-cis-imidazolidinedicarboxylic acid having a pH of at least about 7.5, and (2) a liquid organic phase, and (b) the aqueous solution is acidified to precipitate 2-oxo-1,3-dibenzyl-4,5-cis-imidazolidinedicarboxylic acid and to form an aqueous mother liquor, the invention is the improvement wherein the substantially water-immiscible inert liquid organic solvent is anisole.

It was wholly unexpected that anisole would substantially maintain, and sometimes exceed, the effectiveness of methylene chloride in the process because (1) the chemical structure of anisole is much closer to the structures of toluene and xylene than it is to that of methylene chloride, and (2) the normal boiling point of anisole (about 155° C.) is closer to the normal boiling point of toluene (about 111° C.) and the normal boiling points of the xylene isomers (about 144° C., 139° C., and 138° C. for the ortho, meta, and para isomers, respectively) than it is to the normal boiling point of methylene chloride (about 40° C.), while (3) methylene chloride is more effective as a substantially water-immiscible inert liquid organic solvent than toluene or xylene for the reasons discussed above. In addition, the recovery of anisole from the process is better than that of methylene chloride because the normal boiling point of anisole is much higher than that of methylene chloride.

The alkali metal salt of meso-2,3-bis(benzylamino)succinic acid present in the multi-phase system may be the monoalkali metal salt, the dialkali metal salt, or a mixture of the two. Although it is not desired to be bound by any theory, it is believed that at the rather high values of pH which normally prevail, the alkali metal salt is essentially the dialkali metal salt.

The amount of alkali metal salt of meso-2,3-bis(benzylamino)succinic acid initially present in the liquid aqueous phase of the multi-phase system on a phosgene-free basis may vary widely. In most cases however, the amount of alkali metal salt of meso-2,3-bis(benzylamino)succinic acid initially present in such aqueous phase on a phosgene-free basis is at least about 1 percent by weight. The liquid aqueous phase may, when desired, be initially saturated with respect to alkali metal salt of meso-2,3-bis(benzylamino)succinic acid under the prevailing conditions. Frequently the amount of the alkali metal salt initially present in the aqueous phase on a phosgene-free basis is in the range of from about 5 to about 20 percent by weight. An amount in the range of from about 10 to about 18 percent by weight is preferred.

The molar ratio of alkali metal hydroxide to alkali metal salt of meso-2,3-bis(benzylamino)succinic acid initially present in the aqueous phase of the multi-phase system may also vary widely. Ordinarily the molar ratio is at least about 0.1:1. In many cases the molar ratio is in the range of from about 0.1:1 to about 8:1. Often the molar ratio is in the range of from about 0.2:1 to about 6:1. A molar ratio in the range of from about 0.4:1 to about 3:1 is preferred.

The amount of water present in the multi-phase system is susceptible to very wide variation. In general, at least enough water should be present to maintain a liquid aqueous phase in the multi-phase system, yet not so much that no liquid organic phase is present. Usually the water is present in the multi-phase system on a phosgene-free basis in an amount in the range of from about 5 to about 95 percent by weight. Typically the water is present in an amount in the range of from about 25 to about 90 percent by weight of the multi-phase system on a phosgene-free basis. An amount in the range of from about 40 to about 75 percent by weight on a phosgene-free basis is preferred.

Similarly, the amount of anisole present in the multi-phase system may be very widely varied. In general, at least enough anisole should be present to maintain a liquid organic phase in the multi-phase system, yet not so much that no liquid aqueous phase is present. Ordinarily the anisole is present in the multi-phase system on a phosgene-free basis in an amount in the range of from about 1 to about 50 percent by weight. In many cases the anisole is present in an amount in the range of from about 8 to about 35 percent by weight of the multi-phase system on a phosgene-free basis. An amount in the range of from about 10 to about 30 percent by weight on a phosgene-free basis is preferred.

The multi-phase system may be initially established in a variety of ways. One way is to bring the various components together in essentially any order. In most cases, however, the multi-phase system is first established on a phosgene-free basis and phosgene is thereafter introduced to it. While alkali metal salt of meso-2,3-bis(benzylamino)succinic acid may itself be introduced as a component of the multi-phase system, it is usually more convenient to introduce meso-2,3-bis(benzylamino)succinic acid and to form the alkali metal salt in situ by reacting the meso-2,3-bis(benzylamino)succinic acid with a portion of the alkali metal hydroxide introduced.

Any of the alkali metal hydroxides or mixtures of two or more alkali metal hydroxides may be used. Usually, however, sodium hydroxide, potassium hydroxide, or a mixture of sodium hydroxide and potassium hydroxide is employed. Accordingly, the alkali metal salt of meso-2,3-bis(benzylamino)succinic acid may be any of the alkali metal salts or a mixture of such salts. In most cases the alkali metal salt of meso-2,3-bis(benzylamino)succinic acid is the sodium salt of meso-2,3-bis(benzylamino)succinic acid or the potassium salt of meso-2,3-bis(benzylamino)succinic acid, or a mixture thereof. In the case where the salt is or comprises one or more dialkali metal salts, each individual dialkali metal salt may be a simple dialkali metal salt, such as for example, the disodium salt or the dipotassium salt, or it may be a mixed dialkali metal salt such as the sodium potassium salt. Inasmuch as potassium hydroxide is the preferred alkali metal hydroxide, the potassium salt of meso-2,3-bis(benzylamino)succinic acid is also preferred.

Minor amounts of other inert liquid organic solvents can be in admixture with the anisole provided that they do not markedly depreciate the performance of the anisole. It is preferable, however, that the anisole be as pure as reasonably practicable under the circumstances. Generally the anisole is of at least industrial grade purity. In most cases the purity of the anisole is at least about 95 percent by weight. Often the purity is at least about 98 percent by weight. Preferably the purity is at least about 99 percent by weight.

The alkali metal salt of meso-bis(benzylamino)succinic acid, phosgene, and alkali metal hydroxide are reacted under alkaline conditions. In most cases the pH of the aqueous phase is at least about 7.5 during the reaction. Often the pH of the aqueous phase is at least about 9. Usually the pH of the aqueous phase during the reaction is in the range of from about 9 to about 14. Preferably the pH is in the range of from about 10 to about 12. In order to maintain the pH of the aqueous phase in the desired range as the phosgenation progresses, alkali metal hydroxide, usually as an aqueous solution, may be added as necessary. Preferably, an aqueous solution of alkali metal hydroxide is introduced as a separate stream concurrently with most of the phosgene addition.

The amount of phosgene introduced to the phosgenation reaction may be considerably varied. A deficiency, a stoichiometric amount, or an excess, based on the alkali metal salt of meso-2,3-bis(benzylamino)succinic acid initially present in the multi-phase system may be introduced. Ordinarily at least a stoichiometric amount, and preferably an excess, of phosgene is introduced. Typically the molar ratio of phosgene introduced to alkali metal salt of meso-2,3-bis(benzylamino)succinic acid initially present is in the range of from about 0.9:1 to about 20:1. Often the molar ratio is in the range of from about 1:1 to about 10:1. Preferably the molar ratio is in the range of from about 4:1 to about 8:1.

The temperature and pressure during the reaction may be widely varied. Usually the temperature is in the range of from about 0° C. to about 100° C. Temperatures in the range of from about 10° C. to about 50° C. are preferred. The pressure may be subatmospheric, ambient atmospheric, or superatmospheric. In most cases the pressure is at the prevailing ambient atmospheric pressure or slightly higher.

After the phosgene addition has been completed, alkali metal hydroxide is added if necessary to bring the pH of the aqueous solution of the resulting multi-phase mixture to at least about 7.5. Usually the pH of the aqueous solution at this point is at least about 9, and preferably it is at least about 10. In many cases the pH of the aqueous solution is in the range of from about 7.5 to about 14. Often the pH is in the range of from about 9 to about 14. Preferably the pH is in the range of from about 10 to about 12. After the additions have been completed and the pH of the aqueous solution is at the desired value, it is good practice to stir or otherwise agitate the multi-phase mixture until the pH stabilizes. If the pH should drop below the desired value during the agitation period, it may be brought back to the desired value by the addition of alkali metal hydroxide. Agitation is then preferably continued until the pH is stabilized at the desired value. The sequence of alkali metal hydroxide addition and agitation may be repeated as often as necessary until a desired, stabilized pH is obtained.

As in the case of the alkali metal salt of meso-2,3-bis(benzylamino)succinic acid, the alkali metal salt of cyclo acid may be the monoalkali metal salt, the dialkali metal salt, or a mixture of the two. Although it is not desired to be bound by any theory, it is believed that at the rather high values of pH which normally prevail, the alkali metal salt is essentially the dialkali metal salt, each of which may be a simple dialkali metal salt such as the disodium or the dipotassium salt, or it may be a mixed dialkali metal salt such as the sodium potassium salt.

When the phosgene addition has been completed and the pH of the aqueous solution of the multi-phase mixture is at an appropriate value, the aqueous solution of the alkali metal salt of cyclo acid which has been formed is acidified to precipitate cyclo acid. The acidification may be conducted while the aqueous solution is in the presence of the liquid organic phase of the multi-phase mixture, but preferably anisole is removed from the multi-phase mixture prior to acidification. Removal of anisole may be accomplished using a wide variety of methods. Usually liquid-liquid phase separation techniques such as decantation, centrifugation, or withdrawal of the lower layer are employed. Only one removal method may be used or more than one removal method may be employed as desired.

When anisole is removed, it is not necessary that utterly all of the anisole be removed; however, if any liquid organic phase is present, its amount is usually trivial in comparison with the that of the aqueous solution. Ordinarily, the aqueous solution after standing quiescently for a minute or two does not grossly separate into two distinct layers. In many cases the aqueous solution shows only slight cloudiness upon visual inspection. Often the aqueous solution shows no cloudiness upon visual inspection. It is preferred that the anisole be removed to provide an aqueous solution substantially free from association with a liquid organic phase. It is particularly preferred that substantially no anisole be present.

Acidification may be accomplished by combining the aqueous solution of the alkali metal salt of cyclo acid with the acid. In most cases this is done by introducing the acid to the aqueous solution, by introducing the aqueous solution to the acid, or by admixing separate streams of the aqueous solution and the acid. Preferably the aqueous solution is introduced to the acid.

The pH of the aqueous solution is reduced by combining the aqueous solution and the acid to precipitate cyclo acid. Usually the pH is reduced until the pH of the aqueous mother liquor is about 1 or lower. In many cases the pH of the mother liquor is about 0 or lower.

Substantially any acid strong enough to precipitate cyclo acid may be used. In most cases the acid is a strong inorganic acid such as hydrochloric acid, sulfuric acid, or phosphoric acid. The preferred acid is hydrochloric acid. Mixtures of acids may be used when desired. Similarly, anhydrides of one or more of the acids may be used.

Once the pH has been reduced to about 1 or lower, it may optionally be increased to a value in the range of from about 1.1 to about 1.5. This is ordinarily accomplished by addition of alkali metal hydroxide. Any of the alkali metal hydroxides or mixtures of two or more alkali metal hydroxides may be used. Usually, however, sodium hydroxide, potassium hydroxide, or a mixture of sodium hydroxide and potassium hydroxide is employed. Sodium hydroxide is preferred.

The precipitated cyclo acid is separated from the most of the liquid by techniques such as decantation, filtration, or centrifugation. If the anisole has not been removed prior to the acidification of the aqueous solution, the liquid comprises the aqueous mother liquor and the liquid organic phase. If the anisole has been substantially removed prior to the acidification of the aqueous solution, the liquid is the aqueous mother liquor. The wet solid is then normally washed with water and dried. Inasmuch as the product which is acidified contains only small amounts of alkali metal salt of meso-2,3-bis(benzylamino)succinic acid, if any at all, the dried precipitated solid contains correspondingly small amounts of meso-2,3-bis(benzylamino)succinic acid, if any at all. Ordinarily the recovered solid contains less than about 1 percent by weight meso-2,3-bis(benzylamino)succinic acid, and often it contains less than about 0.5 percent by weight of such acid. Preferably the precipitated solid contains less than about 0.3 percent by weight of meso-2,3-bis(benzylamino)succinic acid. It is most preferred that the precipitated solid contain no detactable meso-2,3-bis(benzylamino)succinic acid using ordinary high performance liquid chromatographic methods customarily employed in production analyses of this general type.

The anisole which has been employed during the phosgenation can be recycled for phosgenation of additional alkali metal salt of meso-2,3-bis(benzylamino)succinic acid. If the anisole has not been removed prior to the acidification of the aqueous solution, it can be recovered from the liquid from which the precipitated cyclo acid has been removed. Any known liquid-liquid separation technique can be used for this purpose. If the concentrations and natures of contaminants are such that they do not materially influence performance of the process in an adverse manner, the anisole can be recycled directly. If, however, the contaminants are unacceptably detrimental, they may be removed by any appropriate technique such as for example distillation, before forwarding the anisole for recycling.

Preferably the recycled anisole is anisole which has been separated from the aqueous solution of the alkali metal salt of cyclo acid prior to acidification. As before, if the concentrations and natures of contaminants are such that they do not materially influence performance of the process in an adverse manner, the anisole can be recycled directly. If, however, the contaminants are unacceptably detrimental, they may be removed by any appropriate technique such as for example distillation, before forwarding the anisole for recycling. It is expected that fewer contaminants will be present in the anisole separated before acidification than after because the anisole would not be exposed to highly acidic conditions which would favor hydrolysis, formation of methyl halide and phenol, and other such reactions. Consequently, it is expected that the anisole separated prior to acidification can be recycled more frequently without removal of contaminants than the anisole separated after acidification. This is another reason why separation of anisole prior to acidification is preferred.

The invention is further described in conjunction with the following examples which are to be considered illustrative rather than limiting, and in which all parts are parts by weight and all percentages are percentages by weight unless otherwise specified.

EXAMPLE I

A one-liter, five-necked glass flask was equipped with a mechanical agitator, a thermometer, a pH probe, a 125-milliliter addition funnel, a dip tube for the introduction of gas below the surface of liquid in the flask, a total reflux condenser cooled with a mixture of solid carbon dioxide and acetone. The flask was provided with a water/solid carbon dioxide cooling bath. The outlet from the condenser was attached to an aqueous sodium hydroxide scrubber so that uncondensed gases leaving the system would pass through the scrubber.

The flask was charged with 46.7 grams (0.142 mole) of dry meso-2,3-bis(benzylamino)succinic acid, and then with 246 milliliters of tap water. Agitation was begun and then 57.6 grams of 45 percent aqueous potassium hydroxide solution was charged to the flask. The addition of the potassium hydroxide solution resulted in an exothermic reaction which increased the temperature of the reaction mixture from 20° C. to 28° C. and ultimately resulted in the slurry of meso-2,3-bis(benzylamino)succinic acid in water being converted into a tinted yellow solution of the dipotassium salt of meso-2,3-bis(benzylamino)succinic acid dissolved in aqueous potassium hydroxide. The pH of the solution was about 13.5.

Eighty-nine milliliters of anisole (assay 99% minimum) was charged into the flask to form a multi-phase system comprising a liquid aqueous phase and a liquid organic phase. Phosgene gas was introduced below the surface of the liquid through the dip tube at an approximately constant rate. The pH was allowed to decrease to 11.0±0.3 before the addition of 45 percent aqueous potassium hydroxide solution as a separate stream was begun. Thereafter the rate of addition of 45 percent aqueous potassium hydroxide solution was varied as necessary to maintain the pH at 11.0±0.3 throughout the remainder of the phosgene addition. When the reaction exotherm had warmed the liquid multi-phase system to 33° C., cooling with the water/solid carbon dioxide bath was applied as necessary to maintain the temperature of the liquid multi-phase system in the range of from about 30° C. to about 35° C. Four hours after beginning the addition of phosgene, the additions of phosgene and 45 percent aqueous potassium hydroxide solution were stopped. During that period, 151 grams of phosgene and 363 milliliters of 45 percent aqueous potassium hydroxide solution were added. Thereafter the multi-phase system was agitated for a period of 94 minutes while a further 12 milliliters of 45 percent aqueous potassium hydroxide solution was added in increments to achieve a stable pH of 10.8. One hundred milliliters of tap water was added to the flask. The resulting multi-phase mixture comprised an aqueous solution of the dipotassium salt of cyclo acid and a liquid organic phase.

The multi-phase mixture was cooled to 20° C. and placed in a separatory funnel, where it was allowed to stand quiescently. The multi-phase mixture separated into an upper liquid organic phase, an intermediate liquid aqueous solution, and a lower layer of salt solids. The salt was dissolved by the addition of 50 milliliters of water. The aqueous solution was then substantially separated from the liquid organic phase. The volume of the recovered liquid organic phase, which was primarily anisole, was 73 milliliters.

A two-liter, four-necked glass flask equipped with a mechanical agitator, a thermometer, a pH probe, and a 250-milliliter addition funnel was charged with 250 milliliters of 38 percent hydrochloric acid. Over a period of 28 minutes, the aqueous solution was added to the hydrochloric acid to form a white slurry. During this period the pH remained less than 1. Thereafter 111 milliliters of 30 percent aqueous sodium hydroxide solution was added over a period of 20 minutes to raise the pH to 1.3 while maintaining the temperature below 50° C. The slurry was cooled to 20° C. and filtered in a filter funnel having a medium sintered glass septum. The filter cake was washed four times with 500 milliliter aliquots of tap water and then dried overnight in a hot air oven at about 83° C. to yield 41.2 grams of cream-colored crystals as product. Analysis of the product showed it to contain 92.7 percent by weight cyclo acid, 0.58 percent by weight meso-2,3-bis(benzylamino)succinic acid, and 0.99 percent by weight anisole. Later analysis by another laboratory showed the product to contain 95.5 percent by weight cyclo acid and 0.7 percent by weight meso-2,3-bis(benzylamino)succinic acid.

EXAMPLE II

A one-liter, five-necked glass flask was equipped with a mechanical agitator, a thermometer, a pH probe, a 125-milliliter addition funnel, a dip tube for the introduction of gas below the surface of liquid in the flask, a total reflux condenser cooled with a mixture of solid carbon dioxide and acetone. The flask was provided with a water/solid carbon dioxide cooling bath. The outlet from the condenser was attached to an aqueous sodium hydroxide scrubber so that uncondensed gases leaving the system would pass through the scrubber.

The flask was charged with 46.7 grams (0.142 mole) of dry meso-2,3-bis(benzylamino)succinic acid, and then with 246 milliliters of tap water. Agitation was begun and then 57.6 grams of 45 percent aqueous potassium hydroxide solution was charged to the flask. The addition of the potassium hydroxide solution resulted in an exothermic reaction which increased the temperature of the reaction mixture from 20° C. to 28° C. and ultimately resulted in the slurry of meso-2,3-bis(benzylamino)succinic acid in water being converted into a tinted yellow solution of the dipotassium salt of meso-2,3-bis(benzylamino)succinic acid dissolved in aqueous potassium hydroxide. The pH of the solution was about 13.5.

Eighty-nine milliliters of anisole (assay 99.89%) was charged into the flask to form a multi-phase system comprising a liquid aqueous phase and a liquid organic phase. Phosgene gas was introduced below the surface of the liquid through the dip tube at an approximately constant rate. The pH was allowed to decrease to 11.0±0.3 before the addition of 45 percent aqueous potassium hydroxide solution as a separate stream was begun. Thereafter the rate of addition of 45 percent aqueous potassium hydroxide solution was varied as necessary to maintain the pH at 11.0±0.3 throughout the remainder of the phosgene addition. When the reaction exotherm had warmed the liquid multi-phase system to 33° C., cooling with the water/solid carbon dioxide bath was applied as necessary to maintain the temperature of the liquid multi-phase system in the range of from about 30° C. to about 35° C. Two hours after beginning the addition of phosgene, the addition of phosgene was discontinued for a period of one hour. During this period 5 milliliters of 45 percent aqueous potassium hydroxide solution was added and the pH dropped from 11.3 to 10.8. The additions of phosgene and 45 percent aqueous potassium hydroxide solution were continued for 2 hours, interrupted for 5 minutes, continued for 10 minutes, and then stopped. Since the beginning of phosgene addition, cumulative totals of 152 grams of phosgene and 360 milliliters of 45 percent aqueous potassium hydroxide solution had been added. Thereafter the multi-phase system was agitated for a period of 83 minutes while a further 15 milliliters of 45 percent aqueous potassium hydroxide solution was added in increments to achieve a stable pH of 10.9. The flask was stoppered and set aside for about 19 hours and 20 minutes. One hundred fifty milliliters of tap water was then added to the flask. The resulting multi-phase mixture comprised an aqueous solution of the dipotassium salt of cyclo acid, a liquid organic phase, and salt solids.

The multi-phase mixture was cooled to 20° C. and placed in a separatory funnel, where it was allowed to stand quiescently. The multi-phase mixture separated into an upper liquid organic phase, an intermediate liquid aqueous solution, and a lower layer of salt solids. The salt was dissolved by the addition of 50 milliliters of water. The aqueous solution was then substantially separated from the liquid organic phase. The volume of the recovered liquid organic phase, which was primarily anisole, was 85 milliliters.

A two-liter, four-necked glass flask equipped with a mechanical agitator, a thermometer, a pH probe, and a 250-milliliter addition funnel was charged with 250 milliliters of 38 percent hydrochloric acid. Over a period of 55 minutes, the aqueous solution was added to the hydrochloric acid to form a white slurry. During this period the pH remained less than 1. Thereafter 116 milliliters of 30 percent aqueous sodium hydroxide solution was added over a period of 26 minutes to raise the pH to 1.35 while maintaining the temperature below 50° C. The slurry was cooled to 20° C. and filtered in a filter funnel having a medium sintered glass septum. The filter cake was washed four times with 500 milliliter aliquots of tap water and then dried overnight in a hot air over at about 75° C. to yield 41.3 grams of cream-colored crystals as product. Analysis of the product showed it to contain 94.6 percent by weight cyclo acid, 0.6 percent by weight meso-2,3-bis(benzylamino)succinic acid, and 0.24 percent by weight anisole. Later analysis by another laboratory showed the product to contain 95.5 percent by weight cyclo acid and 0.4 percent by weight meso-2,3-bis(benzylamino)succinic acid.

Although the present invention has been described with reference to specific details of certain embodiments thereof, it is not intended that such details should be regarded as limitations upon the scope of the invention except insofar as they are included in the accompanying claims.

I claim:

1. In a process wherein:
   (a) alkali metal salt of meso-2,3-bis(benzylamino)succinic acid, phosgene, and alkali metal hydroxide are reacted under alkaline conditions and in the presence of water and substantially water-immiscible inert liquid organic solvent in a multi-phase system to form a multi-phase mixture comprising:
   (1) an aqueous solution of alkali metal salt of 2-oxo-1,3-dibenzyl-4,5-cis-imidazolidinedicarboxylic acid having a pH of at least about 7.5, and
   (2) a liquid organic phase, and
   (b) said aqueous solution is acidified to precipitate 2-oxo-1,3-dibenzyl-4,5-cis-imidazolidinedicarboxylic acid and to form an aqueous mother liquor,
   the improvement wherein said substantially water-immiscible inert liquid organic solvent is anisole.

2. The process of claim 1 wherein the amount of anisole present in said multi-phase system on a phosgene-free basis is in the range of from about 1 to about 50 percent by weight.

3. The process of claim 1 wherein anisole is removed from said multi-phase mixture before said aqueous solution is acidified.

4. The process of claim 3 wherein substantially no anisole is present when said aqueous solution is acidified.

5. The process of claim 3 wherein anisole is removed from said multi-phase mixture by liquid-liquid phase separation.

6. The process of claim 3 wherein the removed anisole is recycled.

7. The process of claim 1 wherein said aqueous solution is acidified in the presence of said liquid organic phase.

8. The process of claim 7 wherein precipitated 2-oxo-1,3-dibenzyl-4,5-cis-imidazolidinedicarboxylic acid is removed from most of said aqueous mother liquor and said liquid organic phase.

9. The process of claim 8 wherein anisole is removed from liquid comprising said aqueous mother liquor and said liquid organic phase.

10. The process of claim 9 wherein said anisole is removed from said liquid comprising said aqueous mother liquor and said liquid organic phase by liquid-liquid phase separation.

11. The process of claim 9 wherein the removed anisole is recycled.

12. The process of claim 1 wherein said aqueous solution is acidified by introducing said aqueous solution to acid.

13. The process of claim 12 wherein said aqueous solution is introduced to hydrochloric acid.

14. The process of claim 1 wherein precipitated 2-oxo-1,3-dibenzyl-4,5-cis-imidazolidinedicarboxylic acid is removed from most of said aqueous mother liquor.

* * * * *